United States Patent [19]
Fainberg et al.

[11] 4,022,894
[45] May 10, 1977

[54] STABLE SOLUTION OF BENZTHIAZIDE (3-[BENZYTHIOL METHYL]-6-CHLORO-2H-1,2,4-BENZO-THIADIAZINE-7-SULFONAMIDE 1,1-DIOXIDE) SUITABLE FOR PARENTERAL ADMINISTRATION AND PROCESS OF PREPARATION

[76] Inventors: Samuel M. Fainberg, 4239 Barcelos Drive; Porfirio F. Perez, 4322 Martyridge, both of St. Louis, Mo. 63129

[22] Filed: Mar. 3, 1975

[21] Appl. No.: 554,675

[52] U.S. Cl. .............................................. 424/246
[51] Int. Cl.$^2$ ...................................... A61K 31/54
[58] Field of Search .................................. 424/246

[56] References Cited
OTHER PUBLICATIONS

Chem. Abst. 8th Collective Index–vol. 66–75 (1967–1971) p. 14099s

*Primary Examiner*—Sam Rosen
*Attorney, Agent, or Firm*—Rogers, Eilers & Howell

[57] ABSTRACT

A clear, stable solution of benzthiazide suitable for medical application has benzthiazide dissolved in an aqueous polyethylene glycol vehicle. The solution has a pH in the range of from about 3 to 6. The solution is prepared by mixing the benzthiazide in polyethylene glycol, stirring until the benzthiazide is dissolved, diluting with water, and adjusting the pH to between about 3 to 6. A benzyl alcohol preservative may be added if desired.

16 Claims, No Drawings

STABLE SOLUTION OF BENZTHIAZIDE (3-[BENZYTHIOL METHYL]-6-CHLORO-2H-1,2,4-BENZOTHIADIAZINE-7-SULFONAMIDE 1,1-DIOXIDE) SUITABLE FOR PARENTERAL ADMINISTRATION AND PROCESS OF PREPARATION

BACKGROUND AND SUMMARY OF THE INVENTION

Benzthiazide (3-[Benzylthio) Methyl]-6-Chloro-2H-1, 2,4-Benzothiadiazine-7-Sulfonamide 1,1-Dioxide) is known to be practically insoluble in water. The sodium or potassium salts of this compound are soluble but these aqueous solutions are not sufficiently stable at a pH suitable for the preparation of injections. At much higher pH these solutions are not suitable for intramuscular injection because they often are accompanied by considerable necrotic reactions at the site of the injection. Previously, injectable benzthiazide was prepared for immediate use by the methods disclosed by U.S. Pat. Nos. 3,361,816 and 3,426,130 (incorporated by reference herein). Those methods use lyophylised unstable solutions which are reconstituted for immediate use. These methods have the disadvantage of requiring reconstitution, that is, they require additional time and care of the nurse, physician, veterinarian, etc. who administers the injection, or require the time of an assistant. Lyophylised solutions are not stable enough to be previously prepared and stored as solutions at room temperature. Typical shelf life of the prepared lyophylised solutions is two to three days under refrigeration, though in some instances life can be 30 to 90 days with refrigeration.

I have prepared stable solutions of benzthiazide which are suitable for parenteral administration of this therapeutically important diuretic, and can also be made suitable for other therapeutic methods of administration, such as syrups for peroral administration. The solutions are stable for up to three years or more at room temperature storage. The solutions eliminate the need for on the spot preparations and the time required thereby. The process for the preparation of a clear, stable aqueous solution of benzthiazide is conducted by dissolving the benzthiazide in an effective amount of a polyalkalene glycol and then diluting the solution with a suitable amount of water. Suitable preservatives, such as benzyl alcohol, may be added with the benzthiazide (or after) if multiple dosage containers are to be prepared and the pH of the solution is adjusted to between about 3 to 6 for injection.

Preferred polyalkalene glycols are the polyethylene glycols, particularly those having an average molecular weight of about 300. However, average molecular weights greater or less than 300 may be effectively used. Any polyalkalene glycol which will dissolve benzthiazide in an aqueous solution may be used.

DESCRIPTION OF THE PREFERRED EMBODIMENTS

The invention relates in particular to stable benzthiazide solutions suitable for intra-muscular or intravenous use and for peroral use. The solutions obtained by the application of the invention are extremely stable aqueous solutions. The solutions of the invention remain effective and are stable when stored for up to 2–3 years under normal room temperature conditions. Previous reconstituted lyophilized solutions are not adequate after 30–90 days under refrigerated storage at most.

By benzthiazide we mean (3-[Benzylthio) Methyl]-6-Chloro-2H-1,2,4-Benzothiadiazine-7-Sulfonamide 1,1-Dioxide) having the structural formula

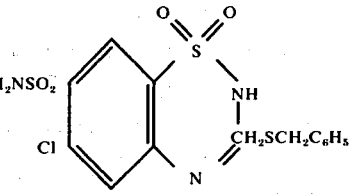

In the solution of the invention typically there will be from about 1 to 5% benzthiazide and from about 45 to 85% polyalkalene glycol. From about 1 to 5% preservative will be used if multiple dosage units are prepared. The balance will be primarily water.

The solutions according to the invention are obtained by dissolving benzthiazide in an effective amount of a suitable polyalkalene glycol such as polyethylene glycol, or a mixture of polyalkalene glycol and water. The preservative is added, if required for multiple dose parenteral preparations, and the pH of the solution is adjusted to a value suitable for injection, e.g., between about 3 and 6 for injection with an effective organic or mineral acid. Suitable preservatives are, for example, benzyl alcohol, sodium formaldehyde sulfoxylate, and phenol. Suitable acids are, for example, hydrochloric acid, sulfuric acid, lactic acid and citric acid.

The following examples are illustrative of the practice of the invention. They are not to be deemed limitative in any respect and other expedients known to those skilled in the art may be employed.

EXAMPLE I

Ten grams of benzthiazide (3-[Benzylthio) Methyl]-6-Chloro-2H-1,2,4-Benzothiadiazine-7-Sulfonamide 1,1-Dioxide) (Pfizer, Inc. Fovane) are added with constant agitation to 450 grams of propylene glycol (average molecular weight 300, Carbowax E300, Dow Chemical Company) and 10 grams of benzyl alcohol. The mixture is stirred constantly for five hours to obtain a clear solution. When all the benzthiazide is dissolved, 500 ml. of distilled water are added, the pH is adjusted to 5 with 2N. hydrochloric acid and the solution adjusted to 1 liter with distilled water for injection. This solution is rendered sterile by filtration and subsequently distributed into suitable injection bottles or ampoules.

EXAMPLE II

Twenty grams of benzyl alcohol and 20 grams of benzthiazide are added with constant agitation to 500 grams of polyethylene glycol. When all the benzthiazide is dissolved, 400 ml. of distilled water are added, the pH is adjusted to 4.5 with 85% lactic acid and the solution adjusted to 1 liter with distilled water for injection. This solution is rendered sterile by filtration and subsequently distributed into suitable injection bottles or ampoules.

EXAMPLE III

Thirty grams of benzthiazide and 30 grams of benzyl alcohol are added with constant agitation to 600 grams of propylene glycol. When all the benzthiazide is dissolved, 300 ml. of distilled water are added, the pH is adjusted to 4.5 with 5N. citric acid and the solution adjusted to 1 liter with distilled water for injection. This solution is rendered sterile by filtration and subsequently distributed into suitable injection bottles or ampoules for single dose use.

EXAMPLE IV

Forty grams of benzthiazide are added with constant agitation to 750 grams of propylene glycol. When all the benzthiazide is dissolved, 40 grams of benzyl alcohol and 150 ml. of distilled water are added and the pH is adjusted to 5.5 with 85% lactic acid and adjusted to 1 liter with distilled water for injection. This solution is rendered sterile by filtration and subsequently distributed into suitable injection bottles or ampoules.

EXAMPLE V

Fifty grams of benzyl alcohol and 50 grams of benzthiazide are added with constant agitation to 850 grams of propylene glycol. When all the benzthiazide is dissolved, 30 ml. of distilled water are added and the pH is adjusted to 5.5 with 2N. hydrochloric acid and adjusted to 1 liter with distilled water for injection. This solution is rendered sterile by filtration and subsequently distributed into suitable injection bottles or ampoules.

EXAMPLE VI

Ten grams of benzyl alcohol and 25 grams of benzthiazide are added with constant agitation to 650 grams of propylene glycol. When all the benzthiazide is dissolved, 250 ml. of distilled water are added and the pH is adjusted to 4.5 with 2N hydrochloric acid and adjusted to 1 liter with distilled water for injection. This solution is rendered sterile by filtration and subsequently distributed into suitable injection bottles or ampoules.

The solution of Example VI has been in room temperature storage test for over one year with no decline in potency and has been in an accelerated storage test for over 3000 hours. The accelerated storage test was conducted at 50° C and is equivalent to three years normal storage. The results of the storage tests are given below.

TABLE I

| | ROOM TEMPERATURE STORAGE | |
|---|---|---|
| AGE MONTHS | BENZTHIAZIDE ASSAY mg./ml. | PERCENT OF INITIAL ASSAY |
| 0 | 28.8 | 100% |
| 3 | 28.9 | 100.3% |
| 6 | 29.3 | 101.7% |
| 9 | 29.2 | 101.3% |
| 12 | 29.1 | 101.0% |

TABLE II

| | ACCELERATED STORAGE | |
|---|---|---|
| AGE HOURS | BENZTHIAZIDE ASSAY mg./ml. | PERCENT OF INITIAL ASSAY |
| 0 | 28.8 | 100% |
| 500 hours | 28.9 | 100.3% |
| 1000 hours | 28.9 | 100% |
| 2000 hours | 28.9 | 100.3% |
| 3000 hours | 28.7 | 99.7% |

The preceding specific embodiments are illustrative of the many experiments which have been conducted within the concepts of the invention. It is to be understood, however, that other expedients, known to those skilled in the art, can be employed or other specific conditions can be used, without departing from the spirit of the invention.

The stable, injectable solutions of benzthiazide disclosed herein are useful as diuretics, particularly for dogs and other small animals, as well as for other uses for which injectable benzethiazide is desired. Dosages for dogs of about 1 to 2 milligrams of benzythiazide per kilogram of body weight would normally be employed where an injectable diuretic was required, for example, where there was severe edema requiring an emergency use of a diuretic to reduce retained fluids.

The description herein is given by way of illustration and not for purposes of limitation. The scope of the invention is to be determined by the attached claims.

We claim:

1. A clear stable solution of benzthiazide suitable for parenteral or peroral administration which comprises benzthiazide dissolved in an effective amount of an aqueous polyalkalene glycol solution and having a pH suitable for injection.

2. The product of claim 1 wherein the solution contains an effective amount of a preservative.

3. The product of claim 2 wherein the preservative is selected from the group consisting of benzyl alcohol, sodium formaldehyde sulfoxylate and phenol.

4. The product of claim 1 wherein the polyalkalene glycol is present in the solution in an amount between about 45 to 85% by weight.

5. The product of claim 1 wherein the pH of the solution is between about 3 and 6.

6. The product of claim 5 wherein the pH is adjusted to between about 3 and 6 with an acid selected from the group consisting of sulfuric acid, hydrochloric acid, lactic acid, and citric acid.

7. The product of claim 1 wherein the polyalkalene glycol is a polyethylene glycol having an average molecular weight of about 300.

8. A method of preparing a clear stable solution of benzthiazide suitable for parenteral or per oral administration comprising dissolving benzthiazide in an effective amount of an aqueous solution of polyalkalene glycol, to form a clear solution, and adjusting the solution to a pH suitable for injection.

9. The method of claim 8 wherein the pH of the solution is adjusted to between about 3 and 6.

10. The method of claim 8 wherein the polyalkalene glycol in the final solvent is between about 45 and 85% by weight of the final solution.

11. The method of claim 8 wherein an effective amount of a preservative is added to the solution.

12. The method of claim 11 wherein the preservative is selected from the group consisting of benzyl alcohol, sodium formaldehyde sulfoxylate, and phenol.

13. The method of claim 8 wherein preservative is added at a level of up to about 5% by weight of the final solution.

14. The method of claim 8 wherein the polyalkalene glycol is a polyethylene glycol having an average molecular weight of about 300.

15. A clear stable solution of benzthiazide suitable for parenteral or peroral administration which comprised an effective amount of benzthiazide for dosage usage dissolved in an aqueous solution of polyalkalene glycol, the polyalkalene glycol being effective to dissolve benzthiazide in the aqueous solution and suitable for parenteral or peroral usage, the stable solution having a pH suitable for injection.

16. The product of claim 15 wherein the polyalkalene glycol is selected from the group consisting of polyethylene glycols and polypropylene glycols having an average molecular weight of about 300.

* * * * *